United States Patent
Erickson et al.

(10) Patent No.: US 12,161,346 B2
(45) Date of Patent: *Dec. 10, 2024

(54) KNEE RESECTION AND GAP BALANCING INSTRUMENTS AND TECHNIQUES FOR KINEMATIC ALIGNMENT

(71) Applicant: Zimmer, Inc., Warsaw, IN (US)

(72) Inventors: Mark D. Erickson, Goshen, IN (US); Edward R. Yager, Fort Wayne, IN (US); Justin J. Kaler, Fort Wayne, IN (US); Ryan Girst, South Bend, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/514,887

(22) Filed: Nov. 20, 2023

(65) Prior Publication Data
US 2024/0081835 A1 Mar. 14, 2024

Related U.S. Application Data

(63) Continuation of application No. 17/318,749, filed on May 12, 2021, now Pat. No. 11,857,202, which is a
(Continued)

(51) Int. Cl.
*A61B 17/15* (2006.01)
*A61B 17/16* (2006.01)
(Continued)

(52) U.S. Cl.
CPC .......... *A61B 17/155* (2013.01); *A61B 17/157* (2013.01); *A61B 17/1675* (2013.01);
(Continued)

(58) Field of Classification Search
CPC ..... A61B 17/15; A61B 17/154; A61B 17/155; A61B 17/157; A61B 2017/564
See application file for complete search history.

(56) References Cited

U.S. PATENT DOCUMENTS 7,510,557 B1 * 3/2009 Bonutti ................. A61F 2/3859
606/86 R
7,615,054 B1 * 11/2009 Bonutti ................. A61B 34/20
606/88

(Continued)

OTHER PUBLICATIONS

"U.S. Appl. No. 16/374,335, Notice of Allowance mailed Feb. 12, 21", 12 pgs.
(Continued)

*Primary Examiner* — Eric S Gibson
(74) *Attorney, Agent, or Firm* — Schwegman Lundberg & Woessner, P.A.

(57) ABSTRACT

Devices and methods for performing total knee arthroplasty procedures with kinematic alignment are described herein. A method of performing a total knee arthroplasty can comprise positioning a femoral cut guide adjacent a distal end of a femur, positioning a tibial cut guide proximate a proximal end of a tibia adjacent an anterior surface of the tibia, adjusting a position of the femoral cut guide and the tibial cut guide relative to each other using a tibial positioning device, fixing the position of the femoral cut guide relative to the tibial cut guide using the tibial positioning device, and resecting the femur and tibia with parallel resections using the femoral and tibial cut guides.

18 Claims, 11 Drawing Sheets

Related U.S. Application Data continuation of application No. 16/374,335, filed on Apr. 3, 2019, now Pat. No. 11,033,281.

(60) Provisional application No. 62/666,615, filed on May 3, 2018.

(51) Int. Cl.
| | | |
|---|---|---|
| *A61B 17/17* | (2006.01) | |
| *A61B 17/56* | (2006.01) | |
| *A61B 17/90* | (2006.01) | |
| *A61B 90/00* | (2016.01) | |

(52) U.S. Cl.
CPC .... *A61B 17/1764* (2013.01); *A61B 2017/564* (2013.01); *A61B 17/90* (2021.08); *A61B 2090/061* (2016.02)

(56) References Cited

U.S. PATENT DOCUMENTS

| | | | | |
|---|---|---|---|---|
| 8,323,288 | B2* | 12/2012 | Zajac | A61B 17/155 |
| | | | | 606/88 |
| 8,419,740 | B2* | 4/2013 | Aram | A61B 17/1764 |
| | | | | 606/88 |
| 9,693,881 | B2 | 7/2017 | Lorio et al. | |
| 10,357,255 | B2* | 7/2019 | Collazo | A61B 17/15 |
| 10,485,553 | B2* | 11/2019 | Uthgenannt | A61B 17/154 |
| 10,568,650 | B2* | 2/2020 | Goble | A61B 17/1764 |
| 10,729,417 | B2* | 8/2020 | Cole | A61B 5/4528 |
| 10,772,617 | B2* | 9/2020 | Cole | A61B 5/1121 |
| 11,033,281 | B2* | 6/2021 | Erickson | A61B 5/4848 |
| 11,857,202 | B2* | 1/2024 | Erickson | A61B 5/6878 |
| 2007/0173946 | A1* | 7/2007 | Bonutti | A61B 17/1717 |
| | | | | 623/20.14 |
| 2008/0147075 | A1* | 6/2008 | Bonutti | A61F 2/3868 |
| | | | | 606/88 |
| 2010/0191244 | A1* | 7/2010 | White | A61F 2/461 |
| | | | | 606/88 |
| 2016/0030053 | A1 | 2/2016 | Yager et al. | |
| 2016/0374699 | A1* | 12/2016 | Fox | A61B 17/1764 |
| | | | | 606/88 |
| 2017/0100132 | A1* | 4/2017 | Collazo | A61B 17/15 |
| 2017/0290597 | A1* | 10/2017 | Goble | A61B 17/1717 |
| 2017/0333018 | A1* | 11/2017 | Sehat | A61B 17/025 |
| 2017/0333212 | A1* | 11/2017 | Wolfson | A61F 2/3859 |
| 2018/0085134 | A1* | 3/2018 | Uthgenannt | A61B 17/1285 |
| 2018/0280038 | A1* | 10/2018 | Goble | A61B 17/1717 |
| 2019/0274696 | A1* | 9/2019 | Goble | A61B 17/155 |
| 2019/0336141 | A1* | 11/2019 | Erickson | A61B 17/157 |
| 2019/0350601 | A1* | 11/2019 | Goble | A61B 90/06 |
| 2020/0155134 | A1* | 5/2020 | Cole | A61B 17/025 |
| 2020/0155135 | A1* | 5/2020 | Cole | A61B 17/8869 |
| 2020/0155168 | A1* | 5/2020 | Minfelde | A61F 2/4684 |
| 2021/0000484 | A1* | 1/2021 | Goble | A61B 17/164 |
| 2021/0259708 | A1* | 8/2021 | Erickson | A61B 5/1072 |

OTHER PUBLICATIONS

"U.S. Appl. No. 17/318,749, Non Final Office Action mailed May 26, 23", 12 pgs.

"U.S. Appl. No. 17/318,749, Notice of Allowance mailed Aug. 21, 23", 9 pgs.

"U.S. Appl. No. 17/318,749, Preliminary Amendment filed Jul. 21, 21", 7 pgs.

"U.S. Appl. No. 17/318,749, Response filed Aug. 2, 2023 to Non Final Office Action mailed May 26, 2023", 13 pgs.

Jackson, Douglas W., et al., "Kinematic vs. mechanical alignment: What is the difference?", Orthopedics Today, (Oct. 2010), 8 pages.

Schiraldi, Marco, et al., "Mechanical and kinematic alignment in total knee arthroplasty", Ann Transl Med 2016;4(7), (Mar. 31, 2016), 5 pages.

\* cited by examiner

KNEE RESECTION AND GAP BALANCING INSTRUMENTS AND TECHNIQUES FOR KINEMATIC ALIGNMENT

CLAIM OF PRIORITY

This application is a continuation of U.S. patent application Ser. No. 17/318,749, filed on May 12, 2021, which is a continuation of U.S. patent application Ser. No. 16/374,335, filed on Apr. 3, 2019, now issued as U.S. Pat. No. 11,033,281, which claims the benefit of U.S. Provisional Patent Application Ser. No. 62/666,615, filed on May 3, 2018, the benefit of priority of each of which is claimed hereby, and each of which is incorporated by reference herein in its entirety.

FIELD

The present subject matter relates to orthopedic procedures and instruments and, more particularly, to bone resection and gap balancing apparatuses and methods for performing total knee arthroplasties with kinematic alignment.

BACKGROUND

Orthopedic procedures and prostheses are commonly utilized to repair damaged bone and tissue in the human body, or replace the damaged bone and tissue if desired. For example, a knee arthroplasty can be used to restore natural knee function by repairing damaged or diseased articular surfaces of the femur or tibia. In a total knee arthroplasty procedure, both the femur and tibia are repaired with prosthetic implants. An incision can be made into the knee joint to expose the bones comprising the joint. Cut guides can be used to guide the removal of the articular surfaces that are to be replaced. Prostheses can be used to replicate the articular surfaces. Knee prostheses can include a femoral component implanted on the distal end of the femur, which articulates with a tibial component implanted on the proximal end of a tibia to replicate the function of a healthy natural knee. Prior to the knee prostheses being selected and implanted, range of motion and other testing can be performed using trial components and other instruments to insure proper prosthesis size and knee joint kinematics. For example, in procedures using mechanical alignment of the femur and tibia, knee balancing can be performed to achieve tension of the ligaments using a knee tensor or balancer. However, other types of alignment and balancing techniques can be performed, with surgeons deciding which techniques to use on a preferential and patient-specific basis.

Overview

The present inventors have recognized, among other things, an opportunity for reducing surgical complexity and improving the precision of surgical resections in total knee arthroplasty procedures, particularly those using kinematic alignment of the femur and tibia, along with the associated benefits to the patient of having better range of motion and comfort. Kinematic alignment of the knee joint involves restoration of the normal three-dimensional orientation of the three axes that describe normal knee kinematics. Current kinematic alignment surgical techniques prescribe utilizing a spacer block or an osteotome to mark an approximate varus resection on the proximal tibia relative to the femur, which can be performed with the knee joint in extension. These are manual processes that are subject to error. For example, sometimes marker lines made or drawn on the tibia against the spacer block or osteotome are difficult to locate and read. Additionally, collateral ligaments may not be properly activated with this free-hand approach. Furthermore, sometimes the surgeon may still desire to balance the knee with a spacer block, which adds complexity and may lead to additional tibial cuts that might result in a non-planar tibia. The present inventors have recognized the difficulties in these processes and have developed devices and techniques that facilitate placement of a proximal tibial resection for precise kinematic alignment. More particularly, the present inventors have recognized that a flexion-first surgical technique can be performed to align a tibial cutting block with a distal femoral cutting block to align the tibia for kinematic restoration relative to the femur utilizing a positioning device. As such, the complexity of the surgical procedure and the likelihood of error can be reduced.

To further illustrate the apparatuses, devices, systems and methods disclosed herein, the following non-limiting examples are provided.

In an example, a method of performing a total knee arthroplasty can comprise positioning a femoral cut guide adjacent a distal end of a femur, positioning a tibial cut guide proximate a proximal end of a tibia adjacent an anterior surface of the tibia, adjusting a position of the femoral cut guide and the tibial cut guide relative to each other using a tibial positioning device, fixing the position of the femoral cut guide relative to the tibial cut guide using the tibial positioning device, and resecting the femur and tibia with parallel resections using the femoral and tibial cut guides.

In another example, a method for coupling a tibial cut guide and a femoral cut guide for performing a total knee arthroplasty with kinematic alignment of a femur and a tibia can comprise attaching a tibial positioning device to a tibial cut guide, attaching the tibial positioning device to a 4-in-1 femoral cut guide, adjusting a position of the tibial cut guide relative to the femoral cut guide to form parallel resections, and immobilizing the tibial cut guide relative to the femoral cut guide using the tibial positioning device.

In yet another example, a total knee arthroplasty positioning system can comprise a tibial positioner device and a tibial cutting guide. The tibial positioner device can comprise a femoral coupling block including first and second laterally spaced coupler pins extending therefrom in a first plane, a tibial coupling block including third and fourth laterally spaced coupler pins extending therefrom in a second plane, and an extension vertically coupling the femoral coupling block and the tibial coupling block such that the first plane and the second plane being parallel to each other. The tibial cutting guide can comprise a tibial guide body, first and second coupling bores extending into the tibial guide body and configured to receive the third and fourth laterally spaced coupler pins, and a cutting surface extending along the tibial guide body in a cutting plane parallel to the second plane.

In still another example, a method of performing resections for kinematic alignment in a total knee arthroplasty can comprise positioning a knee join such that a tibia is located in a flexion position relative to a femur, resecting a distal end of the femur to remove distal-most portions of medial and lateral condyles to form a distal resected surface, coupling a femoral cutting guide to the femur such that a flat posterior surface of the femoral cutting guide is flush with the distal resected surface, coupling a tibial cutting guide to a tibial positioning device, the tibial cutting guide including a proximal tibial cutting guide surface, coupling the tibial positioning device to the femoral cutting guide such that the flat posterior surface of the femoral cutting guide is perpendicular to the proximal tibial cutting guide surface, and resecting a proximal portion of the tibia using the proximal tibial cutting guide surface.

In an additional example, a total knee arthroplasty positioning system can comprise a distal femoral cutting guide having a posterior cutting guide slot, a proximal tibial cutting guide having a proximal cutting guide slot, and a positioner device coupling the distal femoral cutting guide and the proximal tibial cutting guide such that the posterior cutting guide slot and the proximal cutting guide slot are parallel.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices, systems and methods that can be used in a knee replacement procedure, such as a total knee replacement procedure, as well as other types of knee replacement procedures. The present application discloses various assemblies that can be used together as a system for accomplishing portions of the knee replacement procedure, particularly those incorporating kinematic alignment of the tibia and femur. The system can include a tibial positioner device that can connect a distal femoral resection guide attached to a distally resected surface of a femur to a proximal tibial resection guide positioned along an anterior side of an unresected tibia. The tibial positioner device can releasably attach the femoral resection guide and the tibial resection guide such that a proximal tibial resection plane of the tibial resection guide is aligned parallel, or near parallel, to a posterior femoral resection plane of the femoral resection guide, with a desired distance therebetween.

Figure 1:
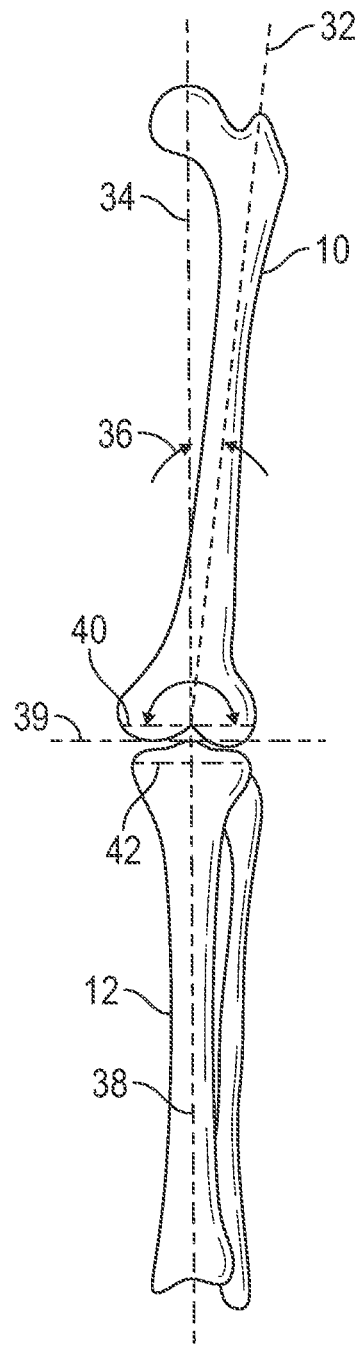
FIG. 1 is a front elevation view of a tibia and a femur showing axes of a knee joint according to example of the present application.
Figure 2:
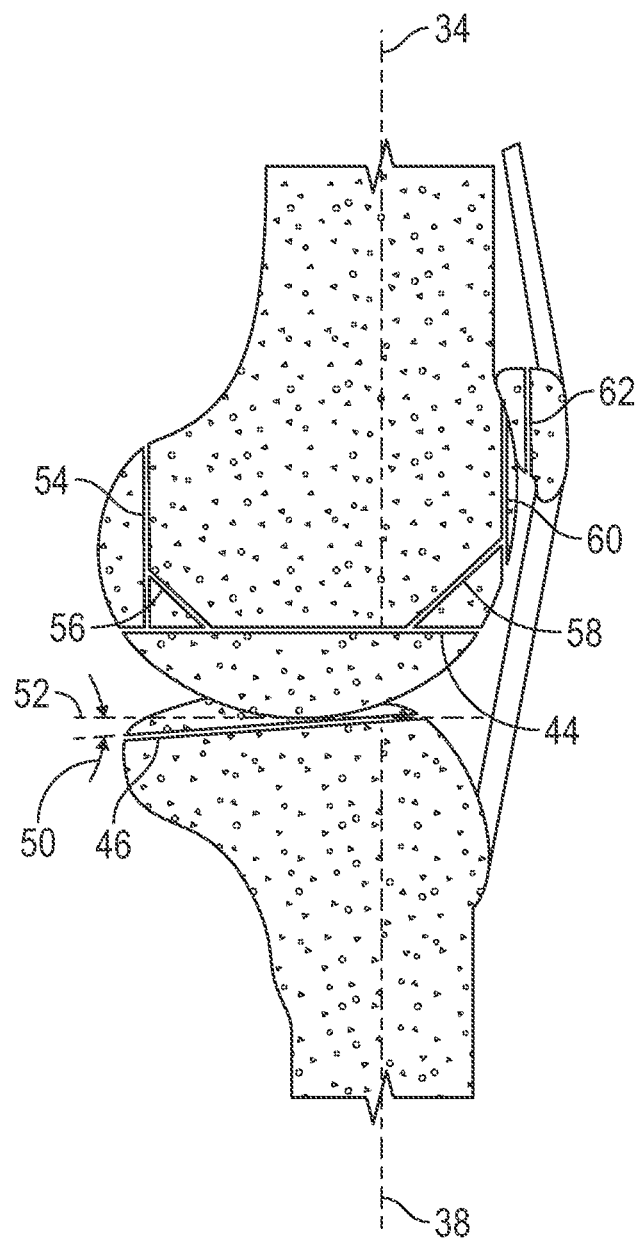
FIG. 2 is a side section view of a knee joint showing typical bone cuts used in replacing the joint surfaces according to examples of the present application.
Figure 3:
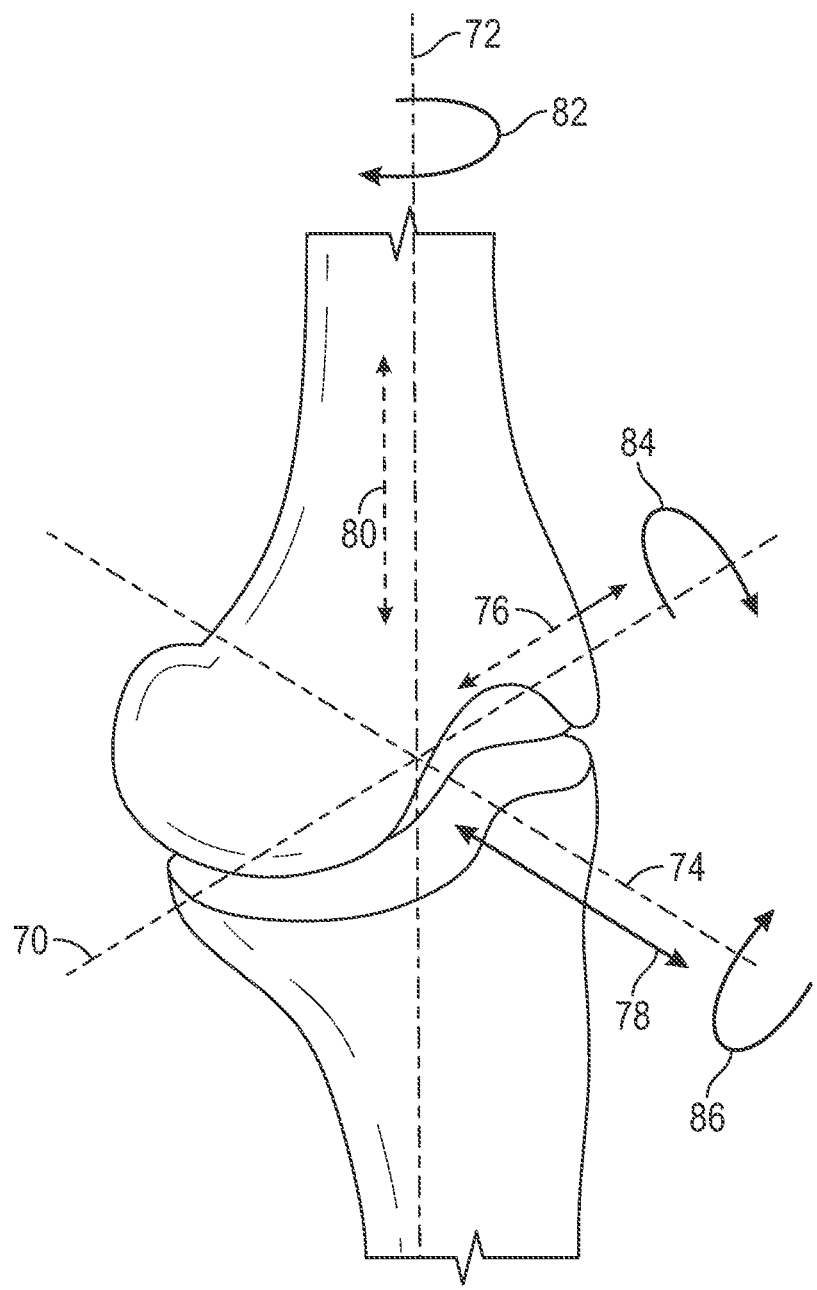
FIG. 3 is a perspective view of a knee joint showing aspects of knee alignment according to examples of the present application.

FIGS. 1-3 illustrate several aspects of a knee joint relevant for implant orientation. FIG. 1 illustrates various axes of the lower limb in the frontal plane. Axes can be defined for each segment of the lower limb. For example, femur 10 has anatomic axis 32 coinciding generally with an associated intramedullary canal. Femur 10 also has mechanical axis 34, or load axis, running from the center of the femoral head to the center of the knee. Angle 36 between these two axes 32, 34 in the frontal plane varies within the patient population but is on the order of 4° to 9°. The two axes 32, 34 are approximately superimposed in the sagittal plane (FIG. 2). Likewise, tibia 12 has mechanical axis 38 coinciding generally with an associated intramedullary canal. Mechanical axis 38 of tibia 12 runs from the center of the knee to the center of the ankle. Transverse axis, or joint line 39, about which the knee flexes, is parallel to a line through the medial and lateral femoral condyles and parallel to the tibial plateau. Typically, the distal femur and proximal tibia are resected to be parallel to joint line 39, and thus perpendicular to mechanical axes 34, 38 as indicated at 40 and 42. The intersection of femoral and tibial mechanical axes 34, 38 may subtend a small angle relative to one another. However, the angle can be small such that axes 34, 38 are approximately collinear and may be treated as collinear for most purposes.

FIG. 2 illustrates the knee joint from the side or sagittal view and various bone cuts that may be made to align implant components. Distal femoral cut 44 is typically made perpendicular to femoral axes 32, 34 in the sagittal plane. Proximal tibial resection 46 is typically cut to match the natural posterior slope, or rotation, of the proximal tibia relative to mechanical axes 34, 38. The amount of posterior to anterior slope 50 relative to reference line 52 perpendicular to mechanical axes 34, 38 varies in the patient population but is on the order of 3°, 5° or 7°, or other values therebetween. In traditional mechanical alignment, this proximal tibial cut should be perpendicular to the mechanical axis, i.e., 0° of varus/valgus. Furthermore, in traditional mechanical alignment, this slope is reproduced via cut blocks with these corresponding slopes built-in. This slope can also be achieved by cutting the proximal tibia at 0° and using implants bearings with the correct slope built into the implant bearings. However, in kinematic alignment, the philosophy calls for more closely matching each patient's individual posterior slope, which may be between 0-7°. The distance between distal femoral cut 44 and proximal tibial cut 46 along mechanical axes 34, 38 is the extension gap. Other cuts may be made depending on the components that are to be implanted. These include posterior femoral cut 54, posterior femoral chamfer cut 56, anterior femoral chamfer cut 58 and anterior femoral cut 60. Patella 62 may also be cut to allow for replacement of the patellar articular surface.

FIG. 3 depicts six aspects of component positioning relative to a coordinate system in which x-axis 70 corresponds approximately to joint line 39, z-axis 72 corresponds approximately to mechanical axes 34 and 38, and y-axis 74 is normal to the other two. Position along each of these axes is depicted by arrows. Position along the x-, y-, and z-axes determines medial/lateral (dx) 76, anterior/posterior (dy) 78, and proximal/distal (dz) 80 positioning of components respectively. Rotation about each of these axes is also depicted by arrows. Rotation about z-axis (rz) 82 corresponds anatomically to external rotation of the femoral component, rotation about x-axis (rx) 84 corresponds to extension plane rotation, and rotation about y-axis (ry) 86 corresponds to varus/valgus rotation.

Primary goals of kinematically aligned TKA are (1) positioning the femoral and tibial components of a knee prosthesis such that the angles and levels of the distal and posterior femoral and tibial joint lines are restored to the patient's natural joint line, (2) restoration of the patient's natural or constitutional alignment prior to the patient having developed osteoarthritis, and (3) restoration of the patient's natural soft tissue laxity and envelope. The kinematically aligned TKA can include a determination of the three kinematic axes illustrated in FIGS. 4A-4C.

Figure 4A:
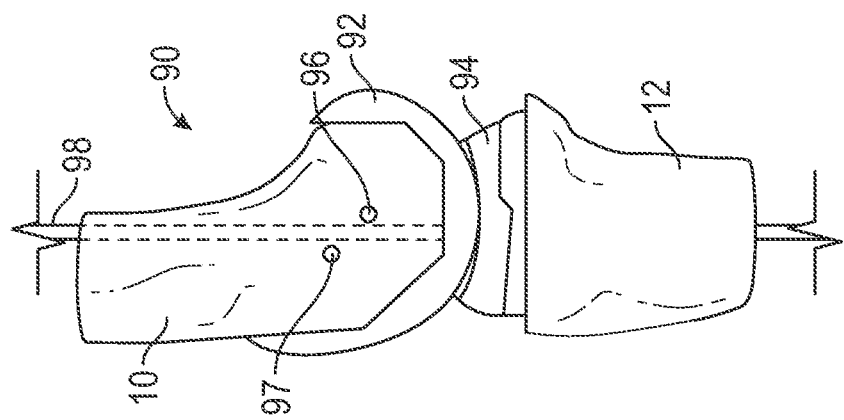
FIG. 4A is an anterior or coronal plane view of a knee joint with an implanted knee prosthesis illustrating three axes of motion for kinematic alignment.
Figure 4B:
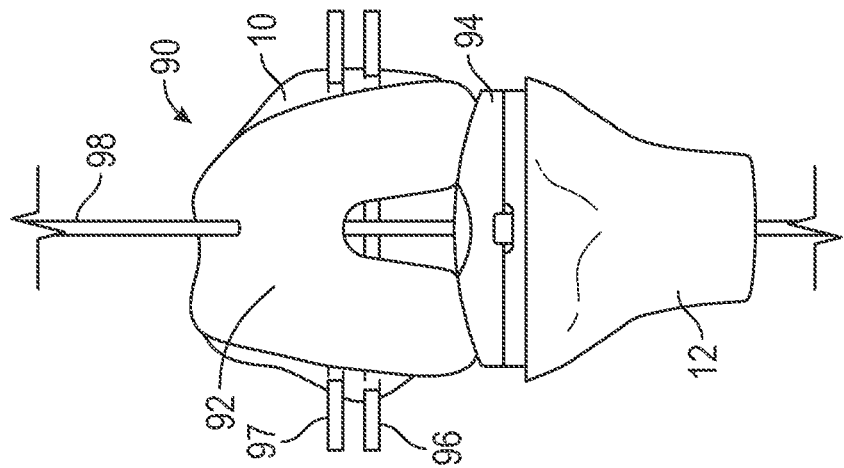
FIG. 4B is an anterior view of the knee joint and knee prosthesis of FIG. 4A in ninety degrees flexion illustrating three axes of motion for kinematic alignment.
Figure 4C:
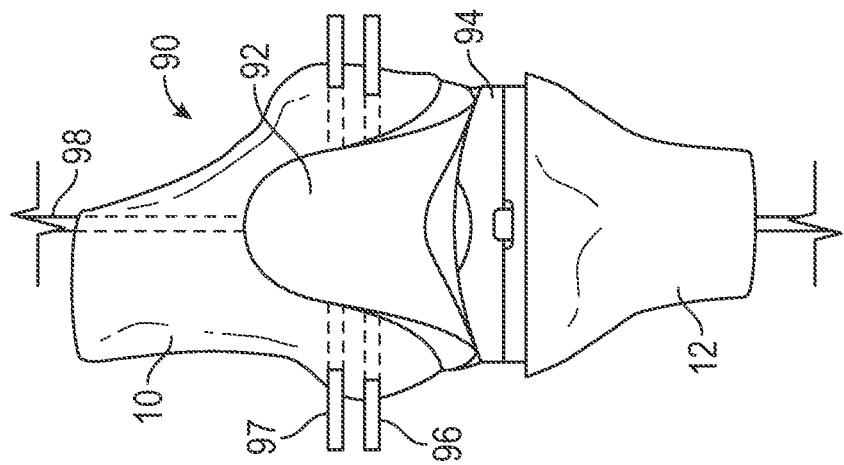
FIG. 4C is a side or sagittal plane view of the knee joint and knee prosthesis of FIGS. 4A and 4B in full extension illustrating three axes of motion for kinematic alignment.

FIGS. 4A-4C show various views of knee prosthesis 90 implanted on a knee joint and illustrate the three kinematic axes of the knee joint in a kinematically aligned TKA. Knee prosthesis 90 can include femoral component 92 implanted on femur 10 and tibial component 94 implanted on tibia 12. A polyethylene surface can be inserted between femur 10 and tibia 12. A kinematically aligned knee includes three axes that describe functional axes of movement about which the knee flexes and rotates. Kinematic alignment considers three-dimensional alignment of the prosthetic femoral and tibial components with respect to the knee instead of two-dimensional alignment of the components with respect to the center of the femoral head and ankle as is done with mechanical alignment. In an example, a femoral component used in kinematic alignment can include symmetric, single-radius condyles on an articular surface. One aspect of kinematic alignment can be to restore normal knee function by aligning the distal and posterior femoral joint line of the femoral component according to the functional femoral transverse axes and joint line of the tibial component to those of the normal knee status.

First kinematic axis 96 can be a transverse axis in femur 10 about which tibia 12 flexes and extends. First kinematic axis 96 can be determined by projecting the lateral and medial femoral condyles of femur 10 onto one another and fitting circles of equal radii over each other. First kinematic axis 96 passes through a center of the circles. Second kinematic axis 97 can be a second transverse axis, parallel to first kinematic axis 96, about which a patella of the knee joint flexes and extends. Second kinematic axis 97 can be located anterior and proximal to first kinematic axis 96. Third kinematic axis 98 is an axis perpendicular to first 96 and second 97 axes about which tibia 12 internally and externally rotates on femur 10.

The methods and devices of the present application facilitate alignment of tibial and femoral resections such that axes 96, 97 and 98 align. For example, a posterior femoral resection can be aligned with a proximal tibial resection to facilitate alignment, such as parallel alignment, of first kinematic axis 96 and second kinematic axis 97.

Figure 5:
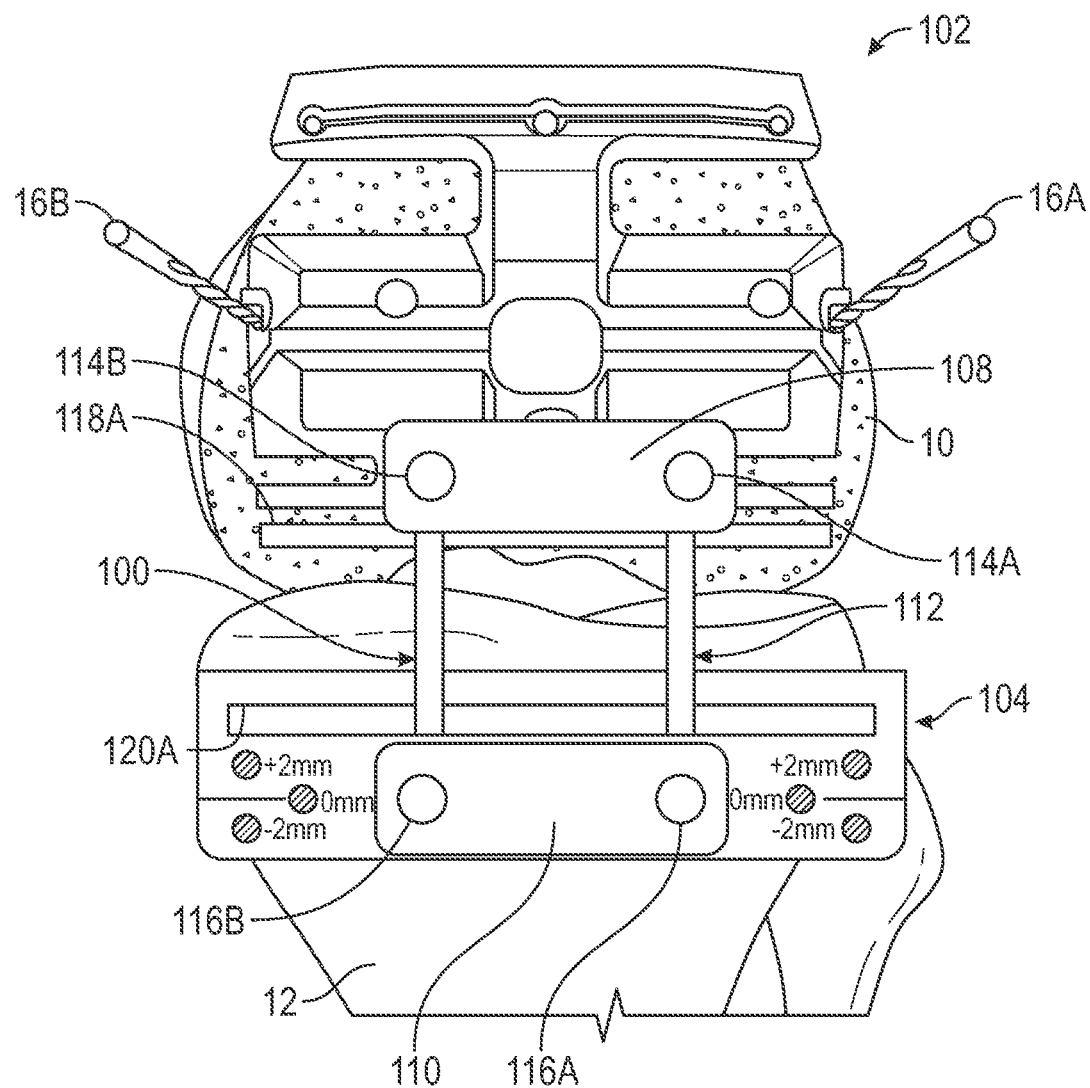
FIG. 5 is a front view of a tibial positioner device according to an embodiment of the present disclosure coupled to femoral and tibial cutting guides for attachment to a femur and a tibia of a knee joint.

FIG. 5 is a front view of tibial positioner device 100 according to an embodiment of the present disclosure coupled to femoral cutting guide 102 and tibial cutting guide 104 for attachment to femur 10 and tibia 12 of a knee joint. Femoral cutting guide 102 can be attached to femur 10 via pins 16A and 16B. Tibial cutting guide 104 can be attached to femoral cutting guide 102 via tibial positioner device 100. Tibial positioner device 100 can comprise femoral coupling block 108, tibial coupling block 110, extension 112, femoral coupling pins 114A and 114B, and tibial coupling pins 116A and 116B. Femoral cutting guide 102 can comprise a plurality of cutting slots, such as posterior cutting slot 118A. Tibial cutting guide 104 can include various cutting slots, such as proximal cutting slot 120A.

Femoral cutting guide 102 and tibial cutting guide 104 can be used to perform resections on femur 10 and tibia 12, respectively, for a total knee arthroplasty (TKA) procedure. Femoral cutting guide 102 and tibial cutting guide 104 can be used to perform TKA procedures with various alignments. For example, guides 102 and 104 can be used for mechanical, kinematic and measured alignment of femur 10 and tibia 12. Tibial positioner device 100 can be used to position tibial cutting guide 104 relative to femoral cutting guide 102 to achieve a desired alignment therebetween. In particular, tibial positioner device 100 can be used to align tibial cutting guide 104 relative to femoral cutting guide 102 for kinematic alignment of femur 10 and tibia 12. For example, tibial positioner device 100, femoral cutting guide 102 and tibial cutting guide 104 can be configured to align proximal cutting slot 120A parallel to posterior cutting slot 118A, as can be desirable in a TKA procedure using kinematic alignment.

Figure 6:
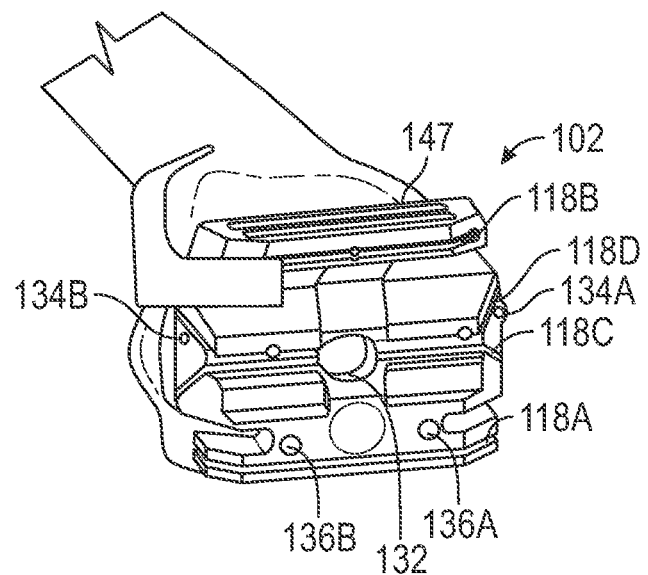
FIG. 6 is an exploded view of the tibial positioner device, the femoral cutting guide and the tibial cutting guide of FIG. 5 showing various components of the devices.
Figure 6:
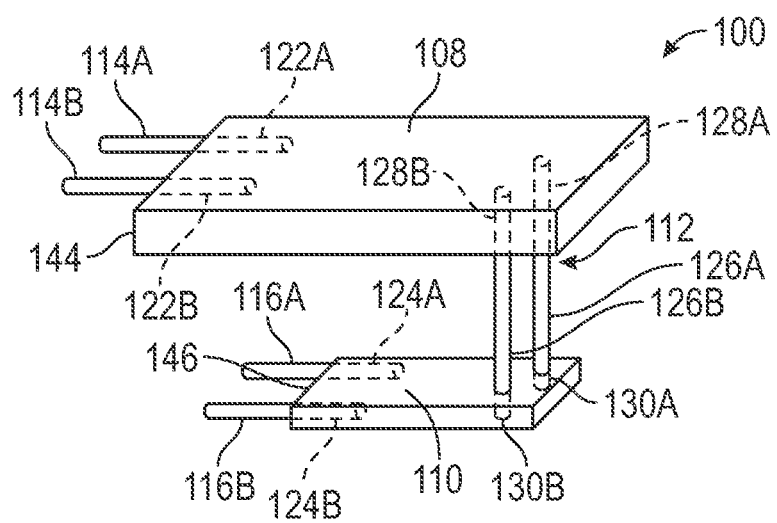
Figure 6:
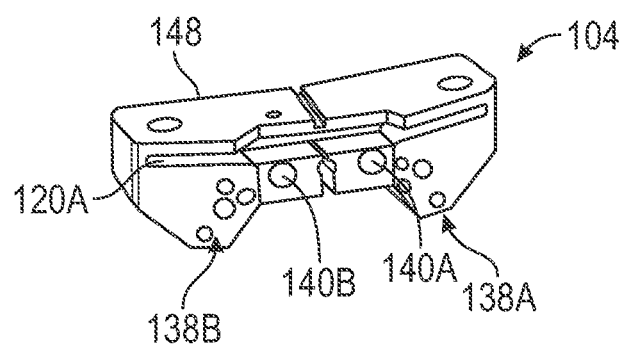

FIG. 6 is an exploded view of tibial positioner device 100, femoral cutting guide 102 and tibial cutting guide 104 of FIG. 5 showing various components of the devices. As mentioned, tibial positioner device 100 can comprise femoral coupling block 108, tibial coupling block 110, extension 112, femoral coupling pins 114A and 114B, and tibial coupling pins 116A and 116B. Femoral coupling block 108 can comprise sockets 122A and 122B for receiving pins 114A and 114B, respectively. Tibial coupling block 110 can comprise sockets 124A and 124B for receiving pins 116A and 116B, respectively.

Extension 112 can comprise extension pins 126A and 126B. Femoral coupling block 108 can also include sockets 128A and 128B, and tibial coupling block 110 can include sockets 130A and 130B. Sockets 128A and 130A can receive extension pin 126A, and sockets 128B and 130B can receive extension pin 126B.

Femoral cutting guide 102 can include posterior cutting slot 118A, anterior cutting slot 118B, posterior chamfer slot 118C, anterior chamfer slot 118D, center bore 132, anchor pin bores 134A and 134B, and mounting bores 136A and 136B.

Tibial cutting guide 102 can include proximal cutting slots 120A, anchor pin bore groupings 138A and 138B, and mounting bores 140A and 140B.

Pins 114A and 114B can be configured to couple to sockets 122A and 122B, respectively. In an example, pins 114A and 114B can be configured to be friction fit within sockets 122A and 122B. Pins 114A and 114B can also be configured to couple to mounting bores 136A and 136B, respectively. In an example, pins 114A and 114B can be configured to freely slide within sockets 136A and 136B.

Pins 116A and 116B can be configured to couple to sockets 124A and 124B, respectively. In an example, pins 116A and 116B can be configured to be friction fit within sockets 124A and 124B. Pins 116A and 116B can also be configured to couple to mounting bores 140A and 140B, respectively. In an example, pins 116A and 116B can be configured to freely slide fit within sockets 140A and 140B.

Pins 126A and 126B can be configured to couple to sockets 128A and 128B and sockets 130A and 130B, respectively. In an example, pins 126A and 126B can be configured to be friction fit within sockets 128A, 128B, 130A and 130B. However, as discussed below, extension 112 can have other configurations. Pins 126A and 126B can be configured to connect block 108 and block 110 in a superior-inferior direction.

Posterior face 144 of femoral coupler block 108 can be configured to mate with femoral cutting guide 102. For example, posterior face 144 can be flat and disposed in a plane perpendicular to the plane extending through the centers of sockets 122A and 122B. As such, a flat posterior face 144 can mate flush against a flat face of femoral cutting guide 102 and a surgeon can have a visual indication that femoral coupler block 108 is properly connected o femoral cutting guide 102.

Posterior face 146 of tibial coupler block 110 can be configured to mate with tibial cutting guide 104. For example, posterior face 146 can be flat and disposed in a plane perpendicular to the plane extending through the centers of sockets 124A and 124B. As such, a flat posterior face 146 can mate flush against a flat face of tibial cutting guide 104 and a surgeon can have a visual indication that tibial coupler block 110 is properly connected o tibial cutting guide 104.

When tibial coupler block 110 and femoral coupler block 108 are attached, posterior face 146 can be offset from posterior face 144 in an anterior-posterior direction toward extension 112, which can permit femoral cutting guide 102 to be positioned above tibia 12 and back against planar distal femoral surface 186, while tibial cutting guide 104 is positioned anterior of the proximal end of tibia 12, as shown below in FIG. 14.

Figure 11:
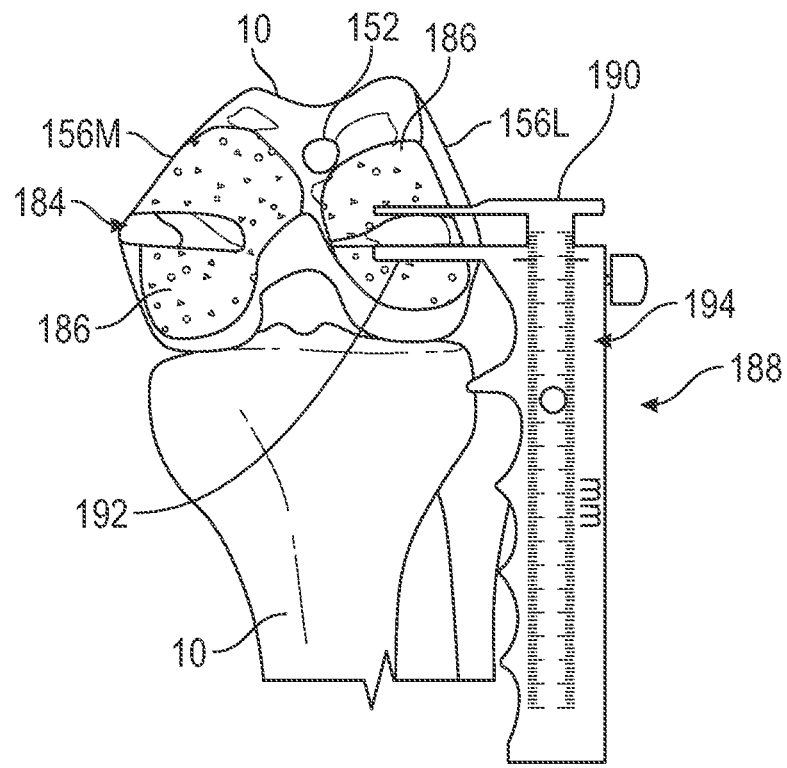
FIG. 11 is a front view of the distally resected femur and a caliper device shown measuring a thickness of resected condyle bone.

Femoral cutting guide 102 can have posterior face 147 that is configured to mate with femur 10. For example, posterior face 147 can be flat to mate flush against planar distal femoral surface 186 (FIG. 11). Tibial cutting guide 104 can have posterior face 148 that is configured to mate with tibia 12. For example, forward face 148 can be curved or arcuate to partially wrap around the curvature of the proximal portion of tibia 12.

Figure 7A:
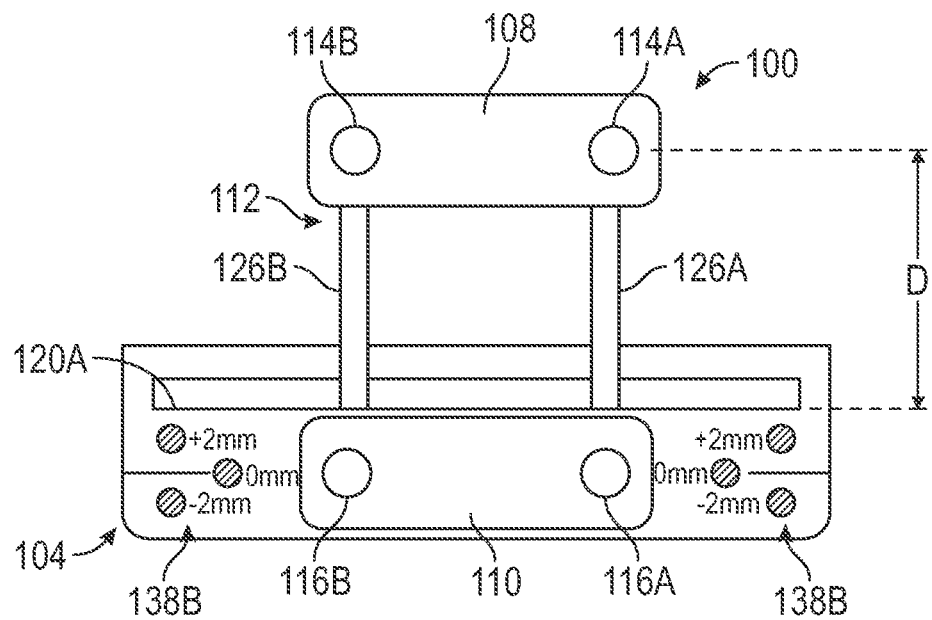
FIG. 7A is a front view of the tibial positioner device of FIGS. 5 and 6 showing extension pins connecting a femoral coupler block and a tibial coupler block.
Figure 7B:
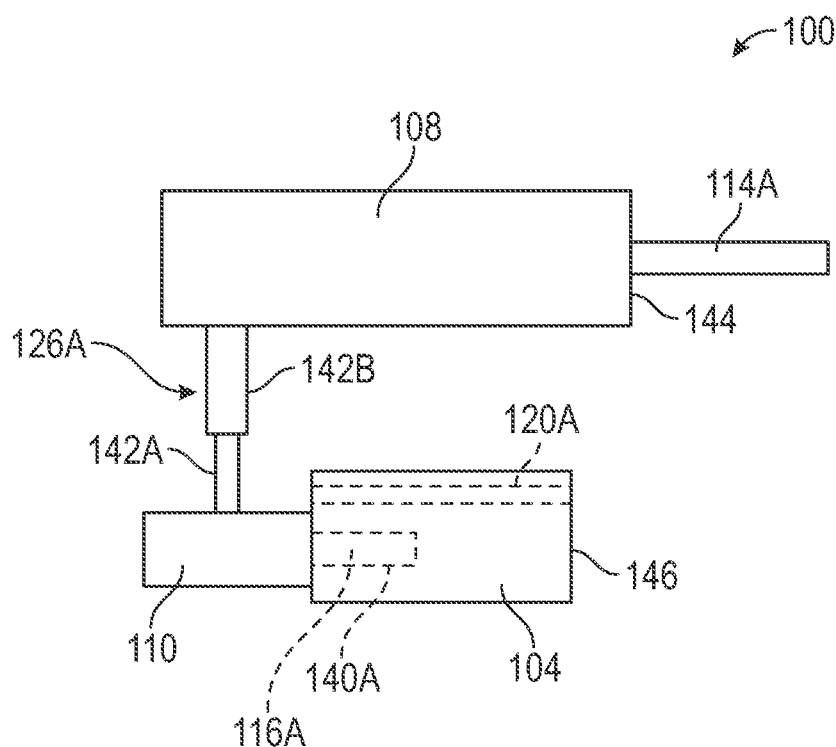
FIG. 7B is a side view of the tibial positioner device of FIG. 7A showing coupler pins for insertion into the femoral cutting guide and the tibial cutting guide.

FIG. 7A is a front view of the tibial positioner device 100 of FIGS. 5 and 6 showing extension pins 126A and 126B connecting femoral coupler block 108 and tibial coupler block 110. FIG. 7B is a side view of tibial positioner device 100 of FIG. 7A showing coupler pins 114A and 116A for insertion into femoral cutting guide 102 and tibial cutting guide 104. FIGS. 7A and 7B are discussed concurrently.

In an example, extension 112 is configured to couple femoral coupler block 108 and tibial coupler block 110 in a desired manner suitable for aligning femoral cutting guide 102 and tibial cutting guide 104 for performing resections for kinematic alignment. Extension 112 can be configured in a variety of ways to either fixedly or adjustably connect block 108 and block 110. In the illustrated embodiment of FIGS. 5-7B, extension 112 can comprise a pair of spaced apart pins, e.g., pins 126A and 126B. Use of two spaced apart pins can prevent relative rotation between femoral coupler block 108 and tibial coupler block 110, as opposed to a single round pin. However, in other embodiments a single pin, post or beam can be used, such as a square post to prevent rotation. In yet other examples, femoral block 108 and tibial block 110 can be connected by C-shaped members or pins to attach to anterior surfaces of blocks 108 and 110 opposite posterior surfaces 144 and 146.

Additionally, in the illustrated embodiment of FIGS. 5-7A, pins 126A and 126B can comprise bodies of a fixed length to fixedly attach block 108 and block 110 to each. In an example, extension 112 is configured to position cutting slot 120A a distance D away from pins 114A and 114B. In an embodiment, distance D can be approximately 19 mm. However, in other embodiments, pins 126A and 126B can be configured to be adjustable in length so that distance D can be adjusted by a surgeon. For example, as illustrated in FIG. 7B, pin 126A (and pin 126B though not visible in FIG. 7B) can be configured to have a telescoping construction where lower pin portion 142A slides into upper pin portion 142B. Pin portions 142A and 142B can be configured with a stop mechanism to incrementally arrest movement of pin portion 142A within pin portion 142B. For example, a detent mechanism can be used. In an example detent mechanism, upper pin portion 142B can be outfitted with a spring-loaded ball bearing that is pushed toward an interior channel of upper pin portion 142B, and lower pin portion 142A can include a series of spaced apart dimples into which the ball bearing can be pushed. Extension 112 can additionally be provided with indicia, such as hash marks, numbering, a scale and the like to indicate the magnitude of distance D.

Extension 112 can be used to balance the knee joint by positioning femoral cutting guide 102 (FIG. 6) with respect to tibial cutting guide 104. In an example for kinematic alignment, extension 112 aligns the plane of pins 114A and 114B with the plane of pins 116A and 116B so that cutting slot 118A of femoral cutting guide 102 (FIG. 6) is parallel to cutting slot 120A of tibial cutting guide 104 so that the knee is balanced with zero degrees of rotation.

FIGS. 8-15 illustrate various method steps that can be used in to perform a total knee arthroplasty procedure using tibial positioner device 100. In various examples, tibial positioner device 100 can be used to perform total knee arthroplasty procedures wherein femoral and tibial prosthetic devices can be implanted for kinematic alignment.

Figure 8:
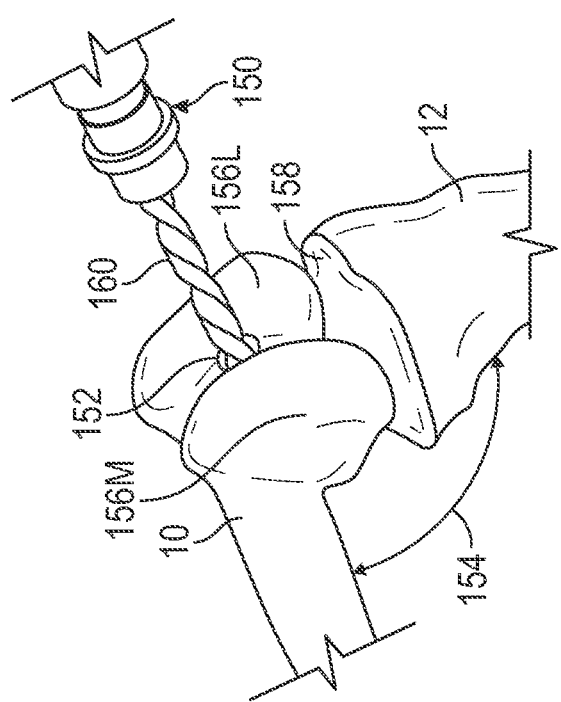
FIG. 8 is a perspective view of a knee joint in flexion with a drilling tool used to produce an intramedullary canal within a femur.

FIG. 8 is a perspective view of a knee joint with tibia 12 in flexion relative to femur 10 with drilling tool 150 used to produce intramedullary canal 152 within femur 10. Femur 10 and tibia 12 can be positioned to produce angle 154 therebetween. In various embodiments, angle 154 can be approximately 90° for a total knee arthroplasty (TKA). Placing the knee joint in flexion facilitates access to medial condyle 156M and lateral condyle 156L of femur 10 and tibial plateau 158 on the proximal portion of tibia 12. As such, distal and anterior cutting guides for femur 10 and proximal cutting guides for tibia 12 can be readily placed onto the knee joint. Drilling tool 150 can comprise any suitable tool for producing intramedullary canal 152 in femur 10. For example, an electric or manual powered drill can be used to couple to and rotate drill bit 160. Drill bit 160 can be rotated by drilling tool 150 to cut through cortical bone between condyles 156M and 156L to penetrate into cancellous bone located in the intramedullary cavity within femur 10. Drilling tool 150 and drill bit 160 can be removed from intramedullary canal 152 such that intramedullary canal 152 can be used to attach other components or devices for the surgical procedure to femur 10.

Figure 9:
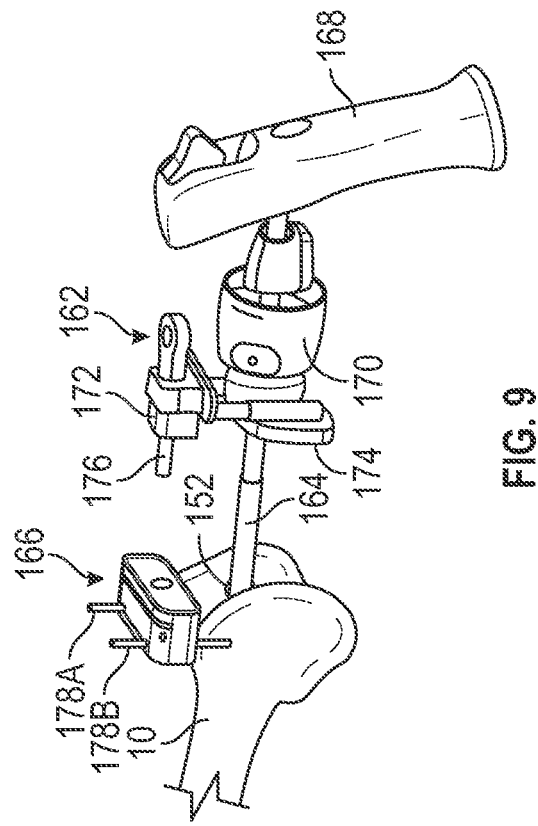
FIG. 9 is a perspective view of a valgus alignment guide coupled to an intramedullary rod disposed within the femur of FIG. 8 used to install a distal femoral cutting guide.

FIG. 9 is a perspective view of valgus alignment guide 162 coupled to intramedullary rod 164 disposed within femur 10 of FIG. 8 that can be used to install distal femoral cutting guide 166. Intramedullary rod 164 can be attached to modular handle 168. Valgus alignment guide 162 can be attached to intramedullary rod 164, and intramedullary rod 164 can be inserted into intramedullary canal 152. Valgus alignment guide 162 can be set to the desired valgus angle from approximately 0° to 9° in embodiments using locking knob 170. Resection tower 172 can be attached to valgus alignment guide 162 for coupling to and positioning of distal femoral cutting guide 166. Resection tower 172 can be adjusted to set the depth for the distal femoral resection to be performed with distal femoral cutting guide 166. Valgus alignment guide 162 can then be pushed to engage flat plate 174 against condyles 156M and 156L. With distal femoral cutting guide 166 attached to rod 176 of resection tower 172, engagement of flat plate 174 with femur 10 can position distal femoral cutting guide 166 to facilitate resection of the distal-most portions of condyles 156M and 156L. Distal femoral cutting guide 166 can be coupled to femur 10 using pins 178A and 178B. In an example, instruments and procedures for placing and attaching distal femoral cutting guide 166 are described in U.S. Pub. No. 2016/0030053 to Yager et al., which is assigned to Zimmer, Inc., the contents of which are hereby incorporated in their entirety by this reference. FIG. 9 illustrates one exemplary scenario, i.e., an example device and procedure, for resecting condyles 156M and 156L, but other scenarios can be used to resect condyles 156M and 156L.

Figure 10:
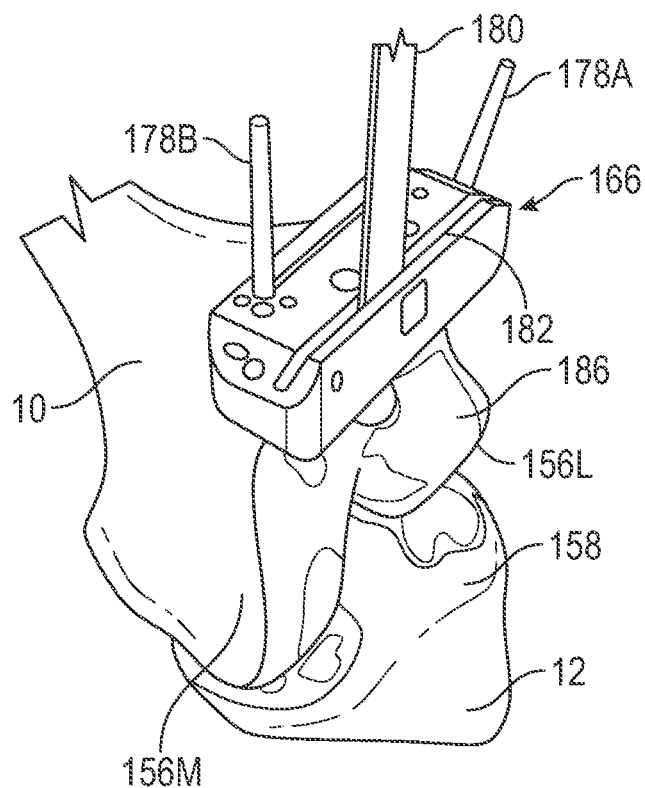
FIG. 10 is a perspective view of a cutting blade inserted into the distal femoral cutting guide of FIG. 9 to resect distal portions of medial and lateral condyles of the femur.

FIG. 10 is a perspective view of cutting blade 180 inserted into cutting slot 182 of distal femoral cutting guide 166 to resect distal portions of medial and lateral condyles 156M and 156L of femur 10. A section, i.e., condyle section 184 of FIG. 11, of the distal end of femur 10 including the distal-most portions of condyles 156M and 156L can be removed from femur 10 to produce planar distal femoral surface 186.

FIG. 11 is a front view of distally resected femur 10 and caliper device 188 shown measuring a thickness of resected bone of condyle section 184. Condyle section 184 is shown positioned in front of planar distal femoral surface 186 rotated ninety-degrees from the orientation in which it was removed. Caliper device 188 can comprise a sliding thickness gauge formed by moveable jaw 190 and fixed jaw 192. Condyle section 184 of femur 10 is shown positioned between fixed jaw 190 and moveable jaw 192 of caliper device 188. Fixed jaw 192 and moveable jaw 190 can function as a thickness gauge, or caliper, that provides an indication of the measured thickness of condyle section 184 using scale 194. Assuming the thicknesses of the distal condyles of the prosthetic femoral component to be sued in the kinematic alignment procedure are 9 millimeters, the resection of a worn condyle should measure approximately 6 mm thick and an unworn condyle should be approximately 8 mm thick (compensating for approximately 1 mm blade thickness). After each of distal medial and lateral condyles 156M and 156L are resected, a thickness of each of the two resected bones can be measured to confirm that the target medial and lateral resection thicknesses were obtained. Alternatively, the first resection can be performed and measured, and then a second resection can be performed and measured to achieve the desired amount of bone removal. FIG. 11 shows caliper device 188 being used, but any tool described herein can be used. Once the desired thickness of condyles 156M and 156L has been achieved, distal femoral cutting guide 166 can be removed from femur 10, such as by withdrawing intramedullary rod 164 from intramedullary canal 152.

Figure 12:
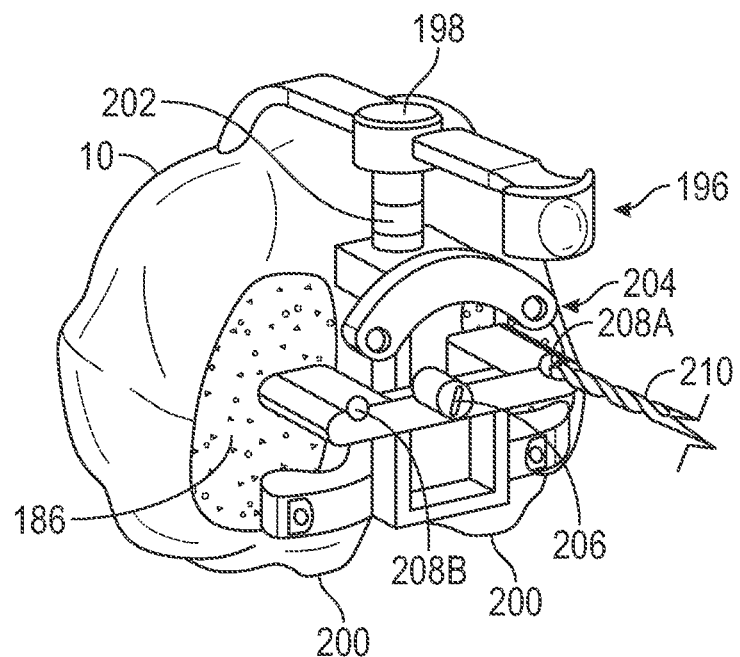
FIG. 12 is a perspective view of a femoral sizer coupled to the distally resected femur to size the femur and prepare holes for mounting a 4-in-1 femoral cutting guide.

FIG. 12 is a perspective view of femoral sizer 196 coupled to distally-resected femur 10 to size femur 10 and prepare holes for mounting a 4-in-1 femoral cutting guide. Femoral sizer 196 can comprise stylus 198, feet 200, slide post 202, rotation body 204 and pivot point 206. Feet 200 can be positioned against posterior surfaces of medial and lateral condyles 156M and 156L and stylus can be positioned against an anterior surface of femur 10 by sliding stylus on slide post 202. Slide post 202 can be provided with indicial to indicate an anterior-posterior size of femur 10. Stylus 198 can be rotated on slide post 202 and can be slid in an inferior-posterior direction to contact femur 10 in a desired location to determine an A-P size for a femoral implant. Additionally, rotation body 204 can be pivoted relative to other components of sizer 196 at pivot point 206 to set a desired rotation for the femoral implant. For exemplary kinematic alignment procedures, the femoral rotation should be, and typically is, set to 0°. With sizer 196 positioned in the desired location and adjusted to the desired settings, holes can be drilled into planar distal femoral surface 186 at drill guide bores 208A and 208B using drill bit 210 and any suitable drilling device. After holes are drilled using drill guide bores 208A and 208B, femoral sizer 196 can be removed from femur 10. In an example, a femoral sizer that can be used in the present procedure is described in U.S. Pat. No. 9,693,881 to Lorio et al., which is assigned to Biomet Manufacturing, LLC, the contents of which are hereby incorporated in their entirety by this reference, can be used to size femur 10. FIG. 12 illustrates one exemplary scenario, i.e., an example device and procedure, for attaching a 4-in-1 cutting guide, but other scenarios can be used to attach a 4-in-1 cutting guide or other cutting guides to femur 10.

Figure 13:
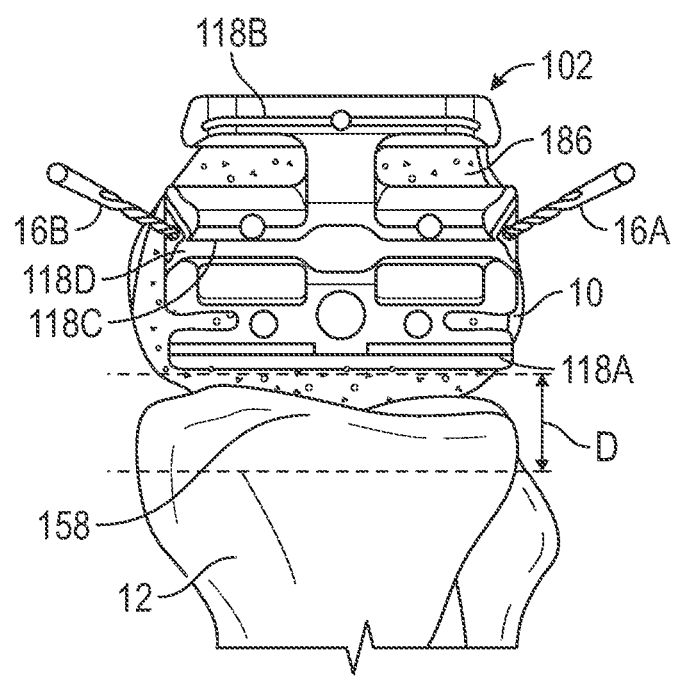
FIG. 13 is a perspective view of a 4-in-1 femoral cutting guide of FIG. 13 shown mounted to a femur and aligned with a proximal end of a tibia.

FIG. 13 is a perspective view of femoral cutting guide 102 shown mounted to femur 10 and aligned with a proximal end of a tibia 12 at tibial plateau 158. In the illustrated embodiment, femoral cutting guide 102 comprises a 4-in-1 cutting guide or block. Pins 16A and 16B can be used to attach femoral cutting guide 102 to planar distal femoral surface 186. For example, pins 16A and 16B can be inserted into anchor pin bores 134A and 134B and into holes in planar distal femoral surface 186 produced using drill guide bores 208A and 208B (FIG. 12). Femoral cutting guide 102 can be used to perform various resections of a distal portion of femur 10 using slots 118A-118D. However, in an example procedure of the present application, further resecting of femur 10 is not performed until after tibial cutting guide 104 (FIG. 14) is placed using femoral cutting guide 102 as a reference via tibial positioner device 100. Thereafter, femur 10 and tibia 12 can be resected in any order.

In exemplary embodiments of procedures described in the present application, it is desirable that the position and location of the proximal resection of tibia 12 be aligned relative to the femoral resections. For kinematic alignment, it can be desirable to reference the proximal tibial resection from the distal posterior femoral resection, such as can be produced by cutting slot 118A. For example, it can be desirable that the proximal tibial resection is parallel to the distal posterior femoral resection and that the proximal tibial resection is spaced from the distal posterior femoral resection a particular distance D. In an example, distance D is approximately 19 mm. However, in other examples, distance D can be greater than 19 mm given specific factors of a particular patient, the particular prosthetic implant devices to be implanted, etc. Previously, distance D was measured with a manual, free-hand process by placing an osteotome or spacer block underneath femoral cutting guide 102. Marking used to indicate where the resection should be placed on tibia 12 were manually placed on tibia 12 and, as such, could be mismarked, erased or obscured by tissue when the resection is finally performed. Tibial positioner device 100 of the present application removes the free-hand process and precisely aligns femoral cutting guide 102 with tibial cutting guide 104.

Figure 14:
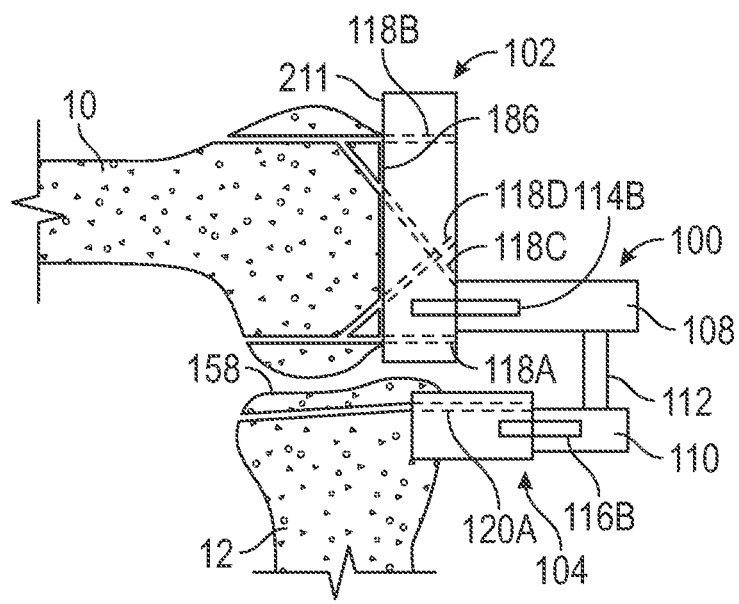
FIG. 14 is a side view of the 4-in-1 femoral cutting guide coupled to a proximal tibial cutting guide via an embodiment of a tibial positioner device of the present application used for kinematic alignment.

FIG. 14 is a side view of 4-in-1 femoral cutting guide 102 coupled to proximal tibial cutting guide 104 via an embodiment of tibial positioner device 100 of the present application. Femoral cutting guide 102 can be attached to femur 10 using pins 16A and 16B, as described above. Tibial positioner device 100 can be attached to proximal tibial cutting guide 104 by inserting pins 116A and 116B into mounting bores 140A and 140B (FIG. 6). Tibial positioner device 100 can, for example subsequently, be attached to femoral cutting guide 102 by inserting pins 114A and 14B into mounting bores 136A and 136B (FIG. 6). As such, cutting slot 120A can be positioned relative to cutting slot 118A by the geometry of tibial positioner device 100. In example configurations, femoral coupling block 108 and tibial coupling block 110 are configured so that pins 114A and 114B will be parallel to pins 116A and 116B. Likewise, mounting bores 136A and 136B of femoral cutting guide 102 can be configured to be parallel to cutting slot 118A, and mounting bores 140A and 140B of tibial cutting guide 102 can be configured to be parallel to cutting slot 120A. As such, when pins 114A and 114B and pins 116A and 116B are used to couple femoral cutting guide 102 and tibial cutting guide 104 via tibial positioner device 100, cutting slots 118A and 120A will be parallel to each other. Additionally, extension 112, pins 114A, 114B, 116A and 116B can position cutting slot 120A perpendicular to posterior surface 211 of femoral cutting guide 102. The length of extension 112 can determine the distance between cutting slots 118A and 120A. As discussed above, extension 112 can be adjustable so that a surgeon can set the distance between cutting slots 118A and 120A to a desired length.

Figure 15:
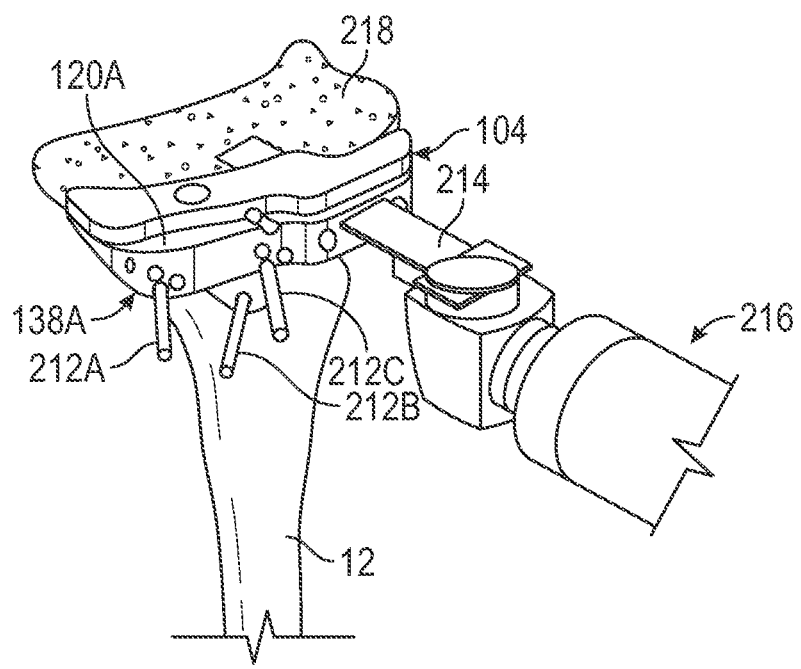
FIG. 15 is a perspective view of the proximal tibial cutting guide of FIG. 14 attached to the tibia via pins and a cutting blade inserted through the proximal tibial cutting guide to resect a proximal portion of the tibia.

FIG. 15 is a perspective view of proximal tibial cutting guide 104 of FIG. 14 attached to tibia 12 via pins 212A, 212B and 212C and cutting blade 214 of cutting device 216 inserted through cutting slot 120A of proximal tibial cutting guide 104 to resect a proximal portion of tibia 12. Pins 212A-212C can be inserted into holes of anchor pin bore groupings 138A to hold tibial cutting guide 104 in place relative to tibia 12. Multiple pins are placed on one side of cutting guide 104 to prevent rotation of cutting guide 104 without interrupting access to cutting slot 120A. Cutting device 216 can comprise any suitable cutting device, such as an oscillating or reciprocating saw device. Blade 214 can be inserted through cutting slot 120A to engage the proximal portion of tibia 12. Blade 214 can be manipulated to remove tibial plateau 158 (FIG. 14) to leave resected tibial surface 218. In an embodiment, resected tibial surface 218 is planar. By using tibial positioner device 100 of the present application, resected tibial surface 218 can be positioned relative to geometry of tibia 12 so that a prosthetic tibial component attached to tibia 12 will kinematically align with a prosthetic femoral component attached to femur 10. In particular, resected tibial surface 218 can be positioned relative to planar distal femoral surface 186 (FIG. 13) so that first kinematic axis 96 and second kinematic axis 97 (FIGS. 4A-4C) will be positioned to the natural joint line of the anatomic femur 10 and tibia 12.

Figure 16:
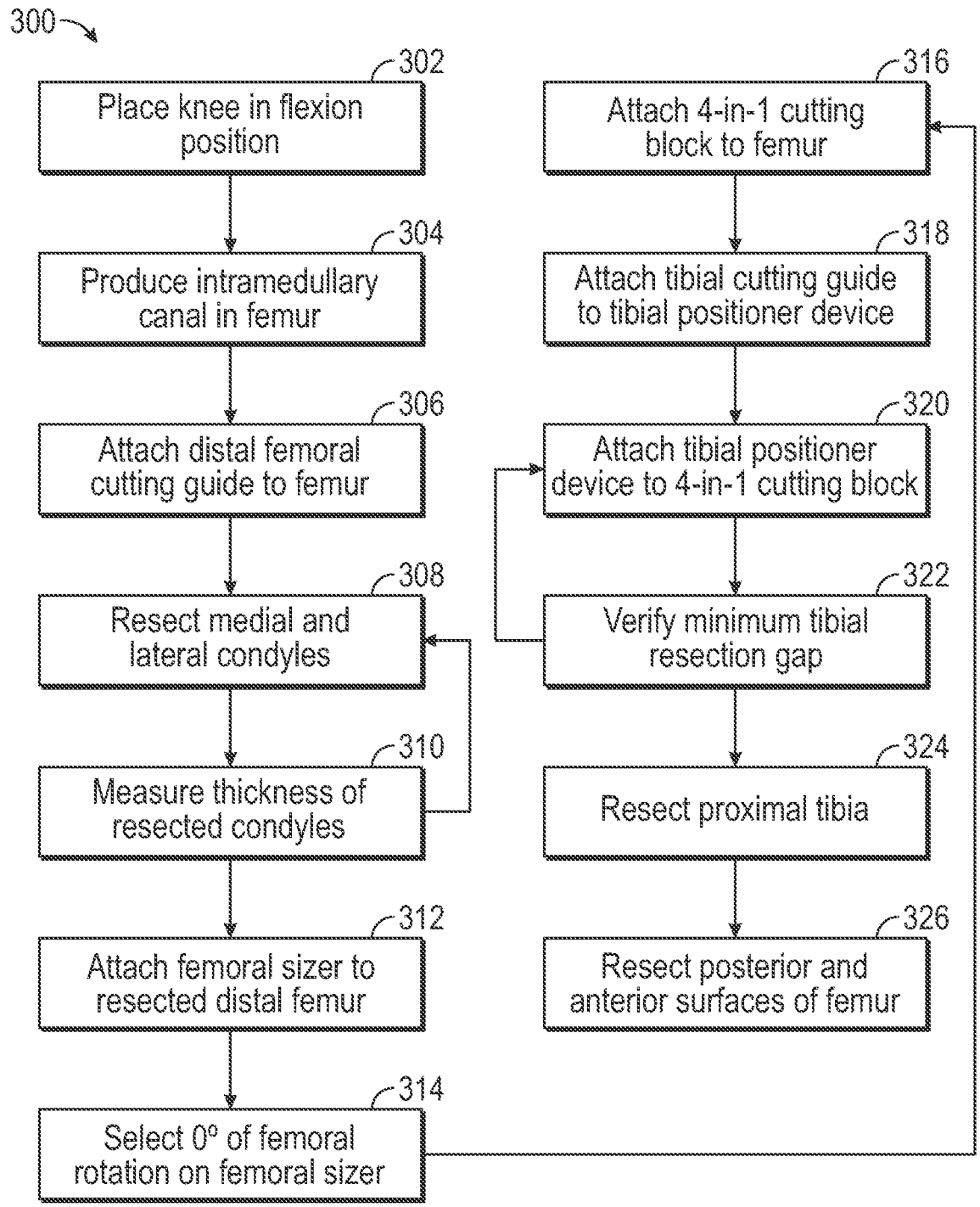
FIG. 16 is a block diagram illustrating an embodiment of a method for preparing a tibia and a femur for a total knee arthroplasty procedure with kinematic alignment.

FIG. 16 shows block diagram 300 illustrating an embodiment of a method for preparing a tibia and a femur for a total knee arthroplasty procedure, particularly one suitable for kinematic alignment of the tibia and femur. At step 302, a knee joint can be positioned in flexion to expose the distal condylar portion of the knee and the proximal anterior portion of the tibia. In an example, the knee joint is put in approximately ninety degrees of flexion. At step 304, an intramedullary canal can be produced in the femur using any suitable method and device. In an example, the intramedullary canal is positioned along the anatomic axis of the femur. The produced intramedullary canal can be suctioned to remove bone debris. At step 306, a distal femoral cutting guide can be attached to the femur. In an example, an intramedullary rod is inserted into the intramedullary canal to facilitate placement of the distal femoral cutting guide. Additionally, a valgus alignment guide can be coupled to the intramedullary rod to position the distal femoral cutting guide and ensure alignment of the distal femoral cutting guide with the anatomy of the femur. At step 308, the distal-most portions of the medial and lateral condyles can be resected. For example, a cutting blade can be inserted through a cutting slot or positioned against a cutting surface of the distal femoral cutting guide to resect the condyles. At step 310, thickness of resected condyles can be measured, such as by using a caliper. It is desirable that the thickness of the resected condyles be at least 6 mm to, for example, ensure proper fit with prosthetic devices. If 6 mm of removed condyle thickness is not obtained, the distal end of the femur can be additionally cut to remove more bone matter. At step 312, a femoral sizer can be attached to the resected distal femur. In examples, an adjustable sizer can be used to find the appropriate femoral size component and also to set the amount of femoral implantation rotation that is desired. The femoral sizer can be used to provide pin placement for a distal femoral cutting guide, such as a 4-in-1 cutting block. At step 314, select 0° of femoral rotation on the femoral sizer. In kinematic alignment procedures the interior-exterior rotation can be, and typically is, set to zero degrees to ensure kinematic axes properly align. In other examples, femoral sizers that are fixed for zero degrees of rotation can be used. At step 316, a 4-in-1 cutting block can be attached to the distally resected surface of the femur. For example, pins placed with the sizer can be used to attach the 4-in-1 cutting block to the femur. At step 318, a tibial cutting guide can be attached to a tibial positioner device, such as ones described with reference to FIGS. 5-7B. At step 320, the tibial positioner device can be attached to the 4-in-1 cutting block to position the tibial cutting guide relative to the tibia and the 4-in-1 cutting block. At step 322, the resection gap between the posterior femoral resection surface and the proximal tibial resection surface can be verified, such as by visual inspection and measurement. If the resection gap is not set to a minimum tibial resection gap distance corrective action can be taken. For example, the anatomy can be adjusted or the tibial cutting guide can be repositioned. In an example, an adjustable tibial positioner device can be adjusted to increase the resection gap. In an example, the minimum tibial resection gap can be 19 mm. At step 324, the proximal tibia can be resected. In an example, the tibial cutting guide can be attached to the tibia with pins and the tibial positioner device can be uncoupled from the tibial cutting guide. Any suitable cutting device can be used. At step 326, posterior and anterior surfaces of the femur can be resected using cutting slots on the 4-in-1 cutting block. In embodiments, the femur can be resected before the tibia is resected, after the tibial positioner device is removed. As discussed, the tibial positioner device can help ensure that the proximal tibial resection is positioned the desired distanced away from the posterior femoral resection. Additionally, the tibial positioner device can help ensure that the proximal tibial resection plane is oriented in the desired orientation relative to the posterior femoral resection plane, such as in a parallel relationship.

VARIOUS NOTES & EXAMPLES

Example 1 can include or use subject matter such as a total knee arthroplasty positioning system that can comprise: a tibial positioner device that can comprise: a femoral coupling block that can include first and second laterally spaced coupler pins extending therefrom in a first plane, a tibial coupling block that can include third and fourth laterally spaced coupler pins extending therefrom in a second plane, and an extension that can vertically couple the femoral coupling block and the tibial coupling block such that the first plane and the second plane being parallel to each other; and a tibial cutting guide that can comprise a tibial guide body, first and second coupling bores that can extend into the tibial guide body and configured to receive the third and fourth laterally spaced coupler pins, and a cutting surface that can extend along the tibial guide body in a cutting plane parallel to the second plane.

Example 2 can include, or can optionally be combined with the subject matter of Example 1, to optionally include first and second laterally spaced coupler pins that can slidably disengage from within the first and second coupling bores.

Example 3 can include, or can optionally be combined with the subject matter of one or any combination of Examples 1 or 2 to optionally include an extension that can comprise first and second extension pins.

Example 4 can include, or can optionally be combined with the subject matter of one or any combination of Examples 1 through 3 to optionally include an extension that can adjustably couple the femoral coupling block and the tibial coupling block.

Example 5 can include, or can optionally be combined with the subject matter of one or any combination of Examples 1 through 4 to optionally include an extension that can position the cutting plane 19 mm below the first and second laterally spaced coupler pins.

Example 6 can include, or can optionally be combined with the subject matter of one or any combination of Examples 1 through 5 to optionally include a tibial cutting guide that can further comprise a plurality of pin-placement bores extending into the tibial guide body and spaced medial-laterally from each other.

Example 7 can include, or can optionally be combined with the subject matter of one or any combination of Examples 1 through 6 to optionally include a posterior face of the tibial guide body that is arcuate.

Example 8 can include, or can optionally be combined with the subject matter of one or any combination of Examples 1 through 7 to optionally include a femoral cutting guide that can comprise a femoral guide body, third and fourth coupling bores extending into the femoral guide body and that can be configured to receive the first and second laterally spaced coupler pins, first, second, third and fourth cutting slots that can extend into the femoral guide body in planes oblique to each other, and first and second pin placement bores that can extend into the femoral guide body spaced medial-laterally from each other.

Example 9 can include, or can optionally be combined with the subject matter of one or any combination of Examples 1 through 8 to optionally include a tibial coupling block that can include a first posterior face from which the first and second laterally spaced coupler pins extend, a femoral coupling block that can include a second posterior face from which the third and fourth laterally spaced coupler pins extend, and an extension that can couple the femoral coupling block and the tibial coupling block such that the first posterior face is anterior-posteriorly offset from the second posterior face toward the extension.

Example 10 can include, or can optionally be combined with the subject matter of one or any combination of Examples 1 through 9 to optionally include a posterior face of the femoral guide body that is flat.

Example 11 can include or use subject matter such as a method of performing resections for kinematic alignment in a total knee arthroplasty that can comprise positioning a knee joint such that a tibia is located in a flexion position relative to a femur, resecting a distal end of the femur to remove distal-most portions of medial and lateral condyles to form a distal resected surface, coupling a femoral cutting guide to the femur such that a flat posterior surface of the femoral cutting guide is flush with the distal resected surface, coupling a tibial cutting guide to a tibial positioning device, the tibial cutting guide including a proximal tibial cutting guide surface, coupling the tibial positioning device to the femoral cutting guide such that the flat posterior surface of the femoral cutting guide is perpendicular to the proximal tibial cutting guide surface, and resecting a proximal portion of the tibia using the proximal tibial cutting guide surface.

Example 12 can include, or can optionally be combined with the subject matter of Example 11, to optionally include a femoral cutting guide that can include a posterior cutting slot disposed in a first cutting plane, a tibial cutting guide that can include a superior cutting slot disposed in a second cutting plane, and coupling the tibial cutting guide and the femoral cutting guide with the tibial positioning device so that the first cutting plane and the second cutting plate are parallel to each other.

Example 13 can include, or can optionally be combined with the subject matter of one or any combination of Examples 11 or 12 to optionally include coupling the tibial positioning device to the femoral cutting guide to position the first cutting plane at least 19 mm away from the second cutting plane.

Example 14 can include, or can optionally be combined with the subject matter of one or any combination of Examples 11 through 13 to optionally include coupling the tibial cutting guide to the tibia using a plurality of pins extending through the tibial cutting guide.

Example 15 can include, or can optionally be combined with the subject matter of one or any combination of Examples 11 through 14 to optionally include removing the tibial positioning device from the tibial cutting guide before resecting the proximal portion of the tibia.

Example 16 can include, or can optionally be combined with the subject matter of one or any combination of Examples 11 through 15 to optionally include resecting the distal end of the femur to remove distal-most portions of the medial and lateral condyles to resect at least 6 mm of condyle from the femur.

Example 17 can include, or can optionally be combined with the subject matter of one or any combination of Examples 11 through 16 to optionally include using an adjustable distal femoral sizer to size an anterior-posterior dimension of the femur before resecting the distal end of the femur, wherein the adjustable distal femoral sizer can be adjusted for zero degrees of external femoral rotation relative to the tibia.

Example 18 can include, or can optionally be combined with the subject matter of one or any combination of Examples 11 through 17 to optionally include resecting a posterior portion of the femur using the femoral cutting guide.

Example 19 can include or use subject matter such as a total knee arthroplasty positioning system that can comprise a distal femoral cutting guide having a posterior cutting guide slot, a proximal tibial cutting guide having a proximal cutting guide slot and a positioner device coupling the distal femoral cutting guide and the proximal tibial cutting guide such that the posterior cutting guide slot and the proximal cutting guide slot are parallel.

Example 20 can include, or can optionally be combined with the subject matter of Example 19, to optionally include a positioner device that can couple the distal femoral cutting guide and the proximal tibial cutting guide such that the posterior cutting guide slot and the proximal cutting guide slot are adjustably offset in a superior-inferior direction.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A total knee arthroplasty positioning system comprising:
   a positioner device comprising:
      a femoral coupling member including first and second spaced coupler bodies extending therefrom in a first plane;
      a tibial coupling member including third and fourth spaced coupler bodies extending therefrom in a second plane; and an extension coupling the femoral coupling member and the tibial coupling member such that the first plane and the second plane are immobilized relative to each other; and a first cutting guide comprising:
a first guide body;
first and second coupling receptacles extending into the first guide body and configured to receive the first and second spaced coupler bodies or the third and fourth spaced coupler bodies; and
a first cutting surface extending along the first guide body in a first cutting plane.

2. The total knee arthroplasty positioning system of claim 1, wherein the third and fourth spaced coupler bodies can disengage from within the first and second coupling receptacles.

3. The total knee arthroplasty positioning system of claim 1, wherein the extension comprises first and second extension bodies.

4. The total knee arthroplasty positioning system of claim 1, wherein the extension adjustably couples the femoral coupling member and the tibial coupling member.

5. The total knee arthroplasty positioning system of claim 1, wherein the extension positions the first cutting plane 19 mm below the first and second spaced coupler bodies.

6. The total knee arthroplasty positioning system of claim 1, wherein the first cutting guide further comprises a plurality of placement receptacles extending into the first guide body, the plurality of placement receptacles being spaced from each other.

7. The total knee arthroplasty positioning system of claim 6, wherein the first cutting guide comprises a tibial cutting guide and the first cutting surface is configured to resect a proximal portion of a tibia.

8. The total knee arthroplasty positioning system of claim 1, further comprising a second cutting guide comprising:
a second guide body;
third and fourth coupling receptacles extending into the second guide body and configured to receive the first and second spaced coupler bodies or the third and fourth spaced coupler bodies, and
a second cutting surface extending along the second guide body in a second cutting plane.

9. The total knee arthroplasty positioning system of claim 8, wherein the second cutting guide comprises a femoral cutting guide and the second cutting surface is configured to resect a distal portion of a femur.

10. The total knee arthroplasty positioning system of claim 1, wherein:
the tibial coupling member includes a first posterior side from which the third and fourth spaced coupler bodies extend;
the femoral coupling member includes a second posterior side from which the first and second spaced coupler bodies extend; and
the extension couples the femoral coupling member and the tibial coupling member such that the first posterior side is anterior-posteriorly offset from the second posterior side toward the extension.

11. A total knee arthroplasty positioning system comprising:
a positioner device comprising:
a femoral coupling member including a femoral coupler body extending in a horizontal direction;
a tibial coupling member including a tibial coupler body extending in the horizontal direction; and
an extension coupling the femoral coupling member and the tibial coupling member in a vertical direction;
wherein the extension comprises a telescoping body that adjustably couples the femoral coupling member and the tibial coupling member; and a first cutting guide comprising:
a first guide body;
a first receptacle extending into the first guide body and configured to receive the femoral coupling member or the tibial coupling member; and
a first cutting surface extending along the first guide body in a first cutting plane.

12. The total knee arthroplasty positioning system of claim 11, further comprising:
a second cutting guide comprising:
a second guide body;
a second receptacle extending into the second guide body and configured to receive the femoral coupling member or the tibial coupling member; and
a second cutting surface extending along the second guide body in a second cutting plane.

13. The total knee arthroplasty positioning system of claim 12, wherein:
posterior-most sides of the first cutting guide and the second cutting guide are offset in an anterior-posterior direction; and
the positioner device is releasably couplable to anterior sides of the first cutting guide and the second cutting guide.

14. The total knee arthroplasty positioning system of claim 11, wherein the extension comprises first and second extension bodies.

15. The total knee arthroplasty positioning system of claim 11, wherein:
the first cutting guide further comprises a plurality of placement receptacles extending into the first guide body; and
the total knee arthroplasty positioning system further comprises a plurality of pins to extend through the plurality of placement receptacles, respectively, to anchor the first cutting guide to bone.

16. The total knee arthroplasty positioning system of claim 11, wherein:
the femoral coupler body comprises a first pair of horizontally spaced pins; and
the tibial coupler body comprises a second pair of horizontally spaced pins.

17. A total knee arthroplasty positioning system comprising:
a femoral cutting guide including a distal femoral cutting guide surface extending into an anterior surface of the femoral cutting guide;
a tibial cutting guide including a proximal tibial cutting guide surface extending into an anterior surface of the tibial cutting guide; and
a positioner for coupling the femoral cutting guide and the tibial cutting guide via attachment to the anterior surfaces of the femoral cutting guide and the tibial cutting guide;
wherein the positioner comprises a viewing gap to allow a knee joint to be viewed between the femoral cutting guide and the tibial cutting guide.

18. The total knee arthroplasty positioning system of claim 17, wherein the positioner maintains the distal femoral cutting guide surface and the proximal tibial cutting guide surface parallel to each other.

* * * * *